(12) United States Patent
Minami

(10) Patent No.: US 9,970,865 B2
(45) Date of Patent: May 15, 2018

(54) DECOMPOSITION DETECTING UNIT, CONCENTRATION MEASURING UNIT, AND CONCENTRATION CONTROL APPARATUS

(71) Applicant: HORIBA STEC, Co., Ltd., Kyoto-shi, Kyoto (JP)

(72) Inventor: Masakazu Minami, Kyoto (JP)

(73) Assignee: HORIBA STEC, CO., LTD., Kyoto-shi, Kyoto (JP)

( * ) Notice: Subject to any disclaimer, the term of this patent is extended or adjusted under 35 U.S.C. 154(b) by 183 days.

(21) Appl. No.: 14/952,735

(22) Filed: Nov. 25, 2015

(65) Prior Publication Data

US 2016/0153898 A1    Jun. 2, 2016

(30) Foreign Application Priority Data

Dec. 2, 2014 (JP) ................................ 2014-244540

(51) Int. Cl.
| | | |
|---|---|---|
| *G01N 21/31* | (2006.01) | |
| *G01N 21/3504* | (2014.01) | |
| *G05D 21/02* | (2006.01) | |
| *G01N 21/84* | (2006.01) | |

(52) U.S. Cl.
CPC ......... *G01N 21/3504* (2013.01); *G05D 21/02* (2013.01); *G01N 2021/8416* (2013.01); *G01N 2201/06113* (2013.01)

(58) Field of Classification Search
None
See application file for complete search history.

(56) References Cited

U.S. PATENT DOCUMENTS

| | | | | | |
|---|---|---|---|---|---|
| 3,995,960 | A | * | 12/1976 | Fletcher | G01N 21/1702 250/343 |
| 4,489,239 | A | * | 12/1984 | Grant | G01N 21/39 250/338.5 |
| 5,026,991 | A | * | 6/1991 | Goldstein | G01N 21/39 250/339.04 |

(Continued)

FOREIGN PATENT DOCUMENTS

JP    2013145887 A    7/2013

*Primary Examiner* — Shawn Decenzo
*Assistant Examiner* — Jarreas C Underwood
(74) *Attorney, Agent, or Firm* — Alleman Hall Creasman & Tuttle LLP

(57) ABSTRACT

Provided is a decomposition detecting unit that despite a simple configuration, can detect whether or not decomposition occurs in material gas resulting from the vaporization of a semiconductor material. The decomposition detecting unit includes: an NDIR type or laser absorption spectroscopy type absorbance measuring mechanism that measures first absorbance, which is absorbance at a wavelength at which a semiconductor material absorbs light, and second absorbance, which is absorbance at a wavelength at which a material produced when the semiconductor material decomposes absorbs light, of mixed gas containing material gas resulting from the vaporization of the semiconductor material; and a decomposition detection part that detects the decomposition in the material gas on the basis of the ratio between first concentration calculated on the basis of the first absorbance and the second absorbance and second concentration calculated on the basis of the second absorbance.

9 Claims, 7 Drawing Sheets

(56) References Cited

U.S. PATENT DOCUMENTS

| | | | | |
|---|---|---|---|---|
| 5,317,156 A * | 5/1994 | Cooper | ............... | G01N 21/39 |
| | | | | 250/339.13 |
| 5,369,278 A * | 11/1994 | Lehto | ............... | G01N 21/274 |
| | | | | 250/343 |
| 5,373,160 A * | 12/1994 | Taylor | ............... | G01N 21/39 |
| | | | | 250/338.5 |
| 5,963,336 A * | 10/1999 | McAndrew | ............... | C23C 16/4412 |
| | | | | 216/60 |
| 6,154,284 A * | 11/2000 | McAndrew | ............... | C23C 16/4412 |
| | | | | 216/60 |
| 6,200,816 B1 * | 3/2001 | Farber | ............... | G01N 33/1813 |
| | | | | 422/62 |
| 6,885,452 B2 * | 4/2005 | McAndrew | ............... | C23C 16/4412 |
| | | | | 216/60 |
| 7,704,301 B2 * | 4/2010 | Zhou | ............... | G01N 21/3504 |
| | | | | 423/210 |
| 7,990,525 B2 * | 8/2011 | Kanda | ............... | G01N 15/1429 |
| | | | | 356/73 |
| 8,008,170 B2 * | 8/2011 | Liang | ............... | H01L 21/0242 |
| | | | | 257/64 |
| 8,903,474 B2 * | 12/2014 | Yaniv | ............... | A61B 5/14551 |
| | | | | 600/475 |
| 9,285,308 B2 * | 3/2016 | Wong | ............... | G01N 21/3504 |
| 2010/0264315 A1 * | 10/2010 | Okada | ............... | G01N 21/3504 |
| | | | | 250/340 |

* cited by examiner

DECOMPOSITION DETECTING UNIT, CONCENTRATION MEASURING UNIT, AND CONCENTRATION CONTROL APPARATUS

TECHNICAL FIELD

The present invention relates to a decomposition detecting unit adapted to detect the decomposition of material gas resulting from the vaporization of a semiconductor material, a concentration measuring unit using the decomposition detecting unit, and a concentration control apparatus.

BACKGROUND ART

In a semiconductor manufacturing process, a solid or liquid semiconductor material is vaporized using a bubbling system, and the vaporized material gas is introduced into a vacuum chamber or the like.

The bubbling system includes: a tank adapted to contain the semiconductor material, an introduction pipe adapted to introduce carrier gas into the tank; and a lead-out pipe adapted to lead out mixed gas containing the carrier gas from the tank and the material gas resulting from the vaporization of the semiconductor material.

The performance and/or quality of semiconductor devices to be manufactured are affected by the concentration of the material gas in the mixed gas introduced into the vacuum chamber. For this reason, the concentration of the material gas in the mixed gas is measured by a concentration meter of some type such as an ultrasonic type or a non-dispersive infrared absorption (NDIR) type provided in the lead-out pipe, and concentration control is performed with a valve provided in the lead-out pipe so as to keep the measured concentration constant at a predetermined value (see Patent Literature 1).

Meanwhile, in the past, relatively stable semiconductor materials such as TEOS have been bubbled and thereby vaporized. However, it is necessary to deposit compound semiconductors in an LED process or a leading-edge Si semiconductor process, and therefore unstable semiconductor materials that include organic metals and easily decompose are also currently used.

For example, in the case where the material gas self-decomposes in the lead-out pipe, a material of a type that is not originally intended is introduced to the vacuum chamber, which may have some effect on the performance and/or quality of semiconductor devices to be manufactured.

Also, the concentration measured by the concentration meter is based on the premise that the mixed gas is configured to contain only the carrier gas and the material gas, and therefore if another material is produced by the self-decomposition of the material gas, errors may occur in concentration measurement and concentration control.

CITATION LIST

Patent Literature

Patent Literature 1: JP-A2013-145887

SUMMARY OF INVENTION

Technical Problem

The present invention is made in consideration of the above-described problems, and intends to provide a decomposition detecting unit that despite a simple configuration, can detect whether or not a semiconductor material decomposes in a material gas resulting from the vaporization of the semiconductor material, a concentration measuring unit using the decomposition detecting unit, and a concentration control apparatus.

Solution to Problem

That is, the decomposition detecting unit of the present invention includes: an NDIR type or laser absorption spectroscopy type absorbance measuring mechanism that measures first absorbance, which is absorbance at a wavelength at which a semiconductor material absorbs light, and second absorbance, which is absorbance at a wavelength at which a material produced when the semiconductor material decomposes absorbs light, of mixed gas containing material gas resulting from the vaporization of the semiconductor material; and a decomposition detection part that detects the decomposition of the semiconductor material on the basis of the first absorbance and the second absorbance.

In such a decomposition detecting unit, the decomposition detection part is configured to detect the decomposition of the semiconductor material on the basis of the first absorbance and the second absorbance, and therefore a change in concentration of the material gas and the occurrence of the decomposition can be distinguished from each other to accurately detect only the decomposition.

More specifically, in the case where the semiconductor material itself absorbs lights having multiple wavelengths, and absorbs a light having the same wavelength as that at which the material produced at the time of the decomposition absorbs light, a value of the second absorbance increases both when the concentration of the material gas increases and when the decomposition occurs. Accordingly, in some cases, monitoring only the value of the second absorbance may make it impossible to detect whether or not the decomposition actually occurs.

Specific configuration examples of the decomposition detection part that can solve such a problem include one where the decomposition detection part is configured to detect the decomposition of the semiconductor material on the basis of a result of comparing the ratio between the first absorbance and the second absorbance measured when the semiconductor material does not decompose and the current ratio between the first absorbance and the second absorbance.

Note that the ratio between the first absorbance and the second absorbance refers to a concept including the case where the second absorbance is zero. Specifically, it is also possible that the ratio between the first absorbance and the second absorbance is 1:0 or the like. Also, the ratio between the first absorbance and the second absorbance may be replaced by a ratio between values to which the absorbances are convertible on a one-to-one basis. For example, the ratio may refer to the ratio between concentrations to which the absorbances are converted.

Further, other specific configuration examples of the decomposition detection part include one where the decomposition detection part is configured to detect the decomposition of the semiconductor material on the basis of a result of comparing the difference between the first absorbance and the second absorbance measured when the semiconductor material does not decompose and the current difference between the first absorbance and the second absorbance.

In addition, the decomposition detection part may be configured to detect the decomposition of the semiconductor material when the increase/decrease tendency of the first absorbance and that of the second absorbance at the same time are different.

In any of such configurations, since the decomposition detection part monitors the ratio or difference between the first absorbance and the second absorbance, or the result of comparing the increase/decrease tendency of the first absorbance and that of the second absorbance, even in the case where a change in concentration of the material gas and the decomposition simultaneously occur, the decomposition of the semiconductor material can be detected. More specifically, when the concentration of the material gas increases, the ratio between the first absorbance and the second absorbance is kept, whereas when the decomposition occurs, only the second absorbance significantly changes, and therefore the ratio between the first absorbance and the second absorbance changes. Accordingly, by monitoring the ratio between the first absorbance and the second absorbance, the decomposition detection part can detect the decomposition of the semiconductor material in the material gas. The same holds true for the case of monitoring the difference between the respective absorbances or the result of comparing the increase/decrease tendency of the first absorbance and that of the second absorbance.

Specific configuration examples that make it harder for the absorbance measuring mechanism to be affected by heat and simplify the configuration of the absorbance measuring mechanism include one where the absorbance measuring mechanism is an NDIR type gas analyzer including: a measuring cell through which the mixed gas passes; a light source part that emits light having a predetermined wavelength bandwidth to the measuring cell; a first filter that among light having passed through the measuring cell, allows the passing of light having the wavelength at which the semiconductor material absorbs light; a second filter that among the light having passed through the measuring cell, allows light having the wavelength at which the material produced when the semiconductor material decompose absorbs light; and a light detection part that detects the light having passed through the first filter or the second filter. Such a configuration example makes it possible to detect the decomposition of the semiconductor material without the use of a large-sized and expensive measuring instrument such as an FTIR spectrometer.

Other configuration examples of the absorbance measuring mechanism include one where the absorbance measuring mechanism is a laser absorption spectroscopy type gas analyzer including: a measuring cell through which the mixed gas passes; a light source part that, to the measuring cell, emits a laser beam having the wavelength at which the semiconductor material absorbs light, and a laser beam having the wavelength at which the material produced when the semiconductor material decomposes absorbs light; and a light detection part that detects the beams having passed through the measuring cell.

Examples of the semiconductor material of which the decomposition easily occurs as compared with before and the second absorbance may be measured regardless of whether or not the decomposition occurs include one where the semiconductor material is organic metal. When applying the present invention to such an example, a change in concentration of the material gas and the occurrence of the decomposition can be distinguished from each other to detect the decomposition, and therefore the effect of the present invention is particularly noticeable.

For example, in order to configure a concentration measuring unit so as to be able to, in a semiconductor process, detect whether or not decomposition occurs and determine whether or not the measured concentration of material gas has a reliable value, it is only necessary that the concentration measuring unit includes: the decomposition detecting unit of the present invention, and a concentration calculation part that on the basis of the first absorbance, calculates first concentration that is the concentration of the material gas in the mixed gas.

In order to make it possible to, when material gas decomposes, stop concentration control just in case, or change the concentration control to concentration control appropriate for the state where the decomposition occurs, it is only necessary that a concentration control apparatus that is used for a bubbling system including: a tank adapted to contain a semiconductor material; an introduction pipe adapted to introduce carrier gas into the tank; and a lead-out pipe adapted to lead mixed gas containing the material gas and the carrier gas out of the tank includes: the above-described concentration measuring unit; a regulation valve that is provided in the lead-out pipe; and a valve control part that controls the regulation valve on the basis of preset target concentration and the measured concentration of the material gas measured by the concentration measuring unit.

In order to add a function that can detect whether or not material gas decomposes using a sensor or the like provided for an existing semiconductor process, it is only necessary to use a decomposition detecting unit program that is a program used for a unit including an NDIR type or laser absorption spectroscopy type absorbance measuring mechanism adapted to measure first absorbance, which is absorbance at a wavelength corresponding to a semiconductor material, and second absorbance, which is absorbance at a wavelength corresponding to a material produced when the semiconductor material decomposes, of mixed gas containing material gas resulting from the vaporization of the semiconductor material, and instructs a computer to function as a decomposition detection part adapted to detect the decomposition of the semiconductor material on the basis of the first absorbance and the second absorbance. In addition, the program may be stored in a storage medium such as a CD, DVD, or flash memory, or electronically delivered through the Internet or the like.

Advantageous Effects of Invention

As described, the decomposition detecting unit of the present invention can detect the decomposition of a semiconductor material only by measuring absorbances at two wavelengths.

DESCRIPTION OF EMBODIMENTS

A decomposition detecting unit 100, concentration measuring unit 200, and concentration control apparatus 300 according to one embodiment of the present invention will be described with reference to FIGS. 1 to 5.

The concentration control apparatus 300 in the present embodiment is one that is used for a semiconductor manufacturing process, and supplies a predetermined concentration of a vaporized semiconductor material to a vacuum chamber where a semiconductor crystal is manufactured by, for example, an MOCVD method (metalorganic chemical vapor deposition method). More specifically, the concentration control apparatus 300 is used for a bubbling system B that supplies carrier gas to the semiconductor material including organic metal to bubble it, and supplies mixed gas of material gas resulting from the vaporization of the semiconductor material and the carrier gas to the vacuum chamber.

Figure 1:
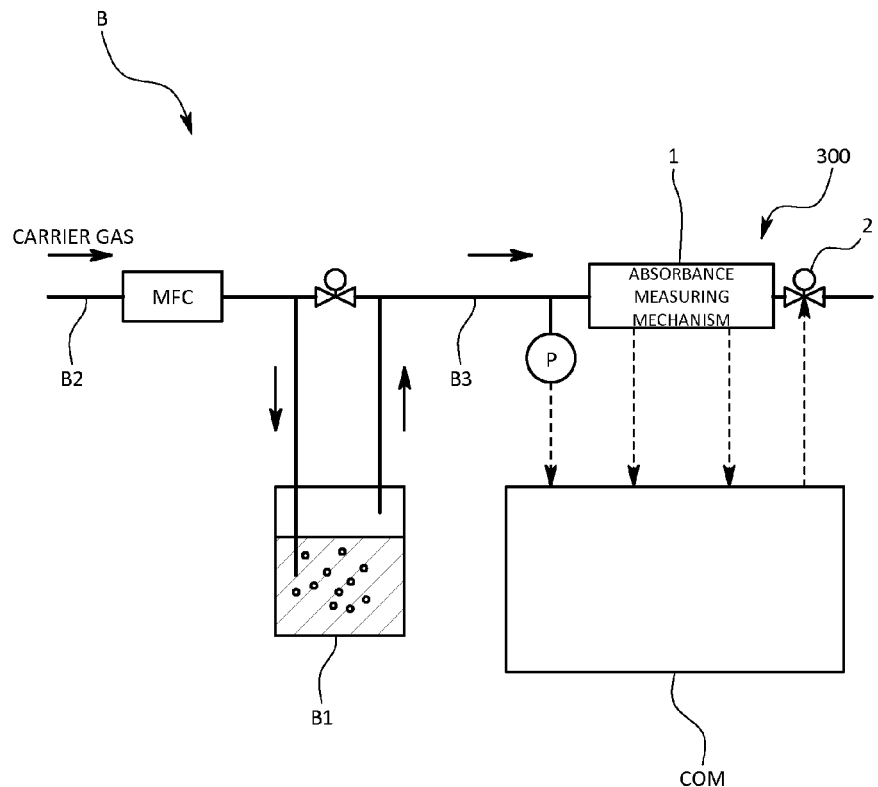
FIG. 1 is a schematic diagram illustrating a concentration control apparatus used for a bubbling system according to one embodiment of the present invention.

As illustrated in FIG. 1, the bubbling system B includes: a tank B1 adapted to contain the semiconductor material; an introduction pipe B2 adapted to supply the carrier gas to the tank B1; and a lead-out pipe B3 that is provided so as to make the connection between the tank B1 and the vacuum chamber, and adapted to lead the mixed gas of the material gas and the carrier gas out of the tank B1 to supply the mixed gas to the vacuum chamber.

The tank B1 contains the semiconductor material, which is liquid in the present embodiment, and the introduction pipe B2 is arranged such that the fore end thereof is positioned below the liquid surface of the semiconductor material. That is, the tank B1 is configured to bubble the semiconductor material by the carrier gas.

The introduction pipe B2 is connected to the supply source of the carrier gas such as nitrogen or hydrogen, and also provided with a mass flow controller for keep the flow rate of the carrier gas supplied into the tank B1 constant.

The lead-out pipe B3 is provided with a pressure sensor P, an absorbance measuring mechanism 1, and a regulation valve 2 sequentially from the upstream side, and these devices and a control mechanism COM adapted to control and operate the respective devices constitute the concentration control apparatus 300. In addition, the control mechanism COM is a so-called computer including a CPU, memory, A/D and D/A converters, input/output means, and the like, and configured to fulfill functions as at least a concentration calculation part 3, decomposition detection part 4, and valve control part 5 by executing a program stored in the memory to make the respective devices cooperate.

In the following, the details of the concentration control apparatus 300 will be described on the basis of a functional block diagram in FIG. 3.

The concentration control apparatus 300 includes: the concentration measuring unit 200 adapted to measure the concentration of the material gas in the mixed gas flowing through the lead-out pipe B3; and the valve control part 5 adapted to control an opening level of the regulation valve 2 on the basis of measured concentration measured by the concentration control apparatus 300 and target concentration.

The concentration measuring unit 200 includes: the decomposition detecting unit 100 adapted to detect the decomposition of the semiconductor material constituting the material gas; and the concentration calculation part 3 adapted to calculate the concentration of the material gas in the mixed gas on the basis of an output of the decomposition detecting unit 100.

More specifically, the decomposition detecting unit 100 includes: the absorbance measuring mechanism 1; and the decomposition detection part 4 adapted to detect the self-decomposition of the material gas on the basis of absorbances measured by the absorbance measuring mechanism 1.

Figure 2:
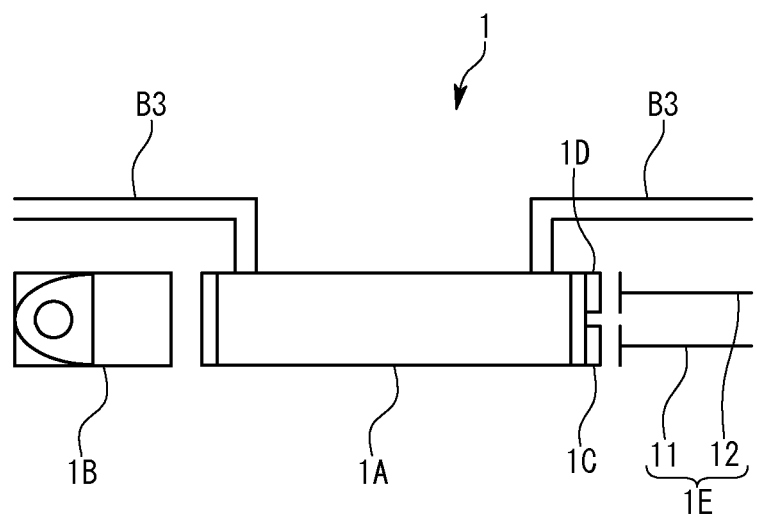
FIG. 2 is a schematic diagram illustrating the details of the absorbance measuring mechanism in the same embodiment.

The absorbance measuring mechanism 1 is an NDIR-based gas analyzer adapted to measure absorbances at two wavelengths or wavelength ranges, and configured to output a signal corresponding to the magnitude of absorbance at each of the wavelengths. In the present embodiment, as illustrated in FIG. 2, the absorbance measuring mechanism 1 is one including a measuring cell 1A, light source part 1B, first filter 1C, second filter 1D, and light detection part 1E.

The measuring cell 1A is a box body provided in the lead-out pipe B3, through which the mixed gas passes. The measuring cell 1A includes: an introduction window through which light emitted from the light source part 1B is introduced; and a lead-out window through which the introduced light is led out toward the light detection part 1E side, and is formed so as to extend with the light traveling direction as its longer direction.

The light source part 1B is a lamp that emits infrared light having a predetermined wavelength bandwidth to the measuring cell 1A, and provided separately from the introduction window of the measuring cell 1A.

The first filter 1C is one that among light having passed through the measuring cell, allows the passing of light having a wavelength at which the semiconductor material absorbs light.

The second filter 1D is one that among the light having passed through the measuring cell, allows the passing of light having a wavelength at which a material produced when the semiconductor material decomposes absorbs light.

The light detection part 1E is one including: a first detector 11 adapted to detect the intensity of the light having passed through the first filter 1C; and a second detector 12 adapted to detect the intensity of the light having passed through the second filter 1D. The light detection part 1E is configured to, on the basis of outputs of the first detector 11 and the second detector 12, output first absorbance that is absorbance at the first wavelength at which the semiconductor material absorbs light, and second absorbance that is absorbance at the second wavelength at which the material produced when the semiconductor material decomposes absorbs light.

To give a more specific description taking as an example the case of using trimethylgallium, which is an organic metal, as the semiconductor material, the absorbance measuring mechanism 1 is adapted to, on the basis of the output of the first detector 11, measure the first absorbance corresponding to the first wavelength that is a main absorption wavelength of trimethylgallium. Also, the absorbance measuring mechanism 1 is adapted to, on the basis of the output of the second detector 12, measure the second absorbance corresponding to the second wavelength that is an absorption wavelength of methane produced when trimethylgallium self-decomposes.

Figure 4A:
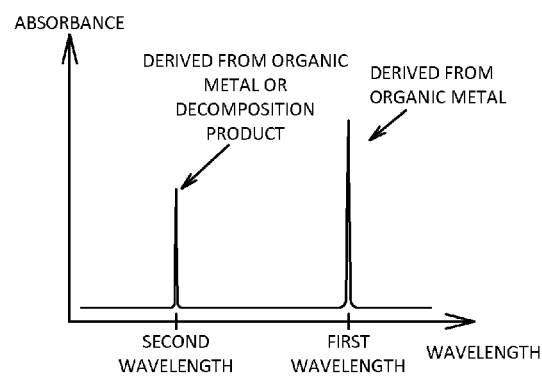
FIGS. 4(a) to 4(c) include schematic graphs for explaining the relationship between absorbances and decomposition in the same embodiment.

Even in the case where self-decomposition does not occur, as illustrated in a spectrum in FIG. 4(a), a semiconductor material including an organic metal such as trimethylgallium may have two absorption wavelength peaks. This is because a methyl group connected to gallium in trimethylgallium vibrates, and thereby a sub-absorption wavelength peak different from a main absorption wavelength peak appears. Also, the methyl group and methane produced by the self-decomposition of trimethylgallium have substantially the same absorption wavelength.

Figure 4B:
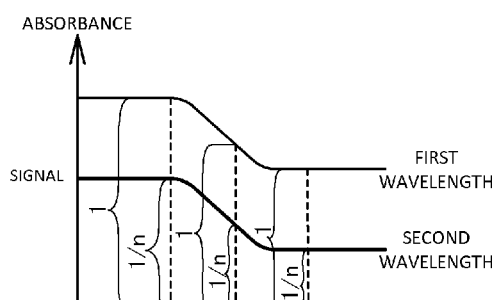

FIG. 4(b) illustrates a graph of pieces of time series data on the first and second absorbances measured when the concentration of the material gas is changed from some concentration to other concentration in a state where the semiconductor material does not self-decompose. When the self-decomposition does not occur, between the first absorbance corresponding to the absorption wavelength of trimethylgallium as an organic metal, and the second absorbance corresponding to the absorption wavelength of arms such as the methyl group, a predetermined ratio of 1:1/n is kept regardless of the concentration of the material gas as illustrated in the graph of FIG. 4(b). That is, in any of an initial state interval where the concentration of the material gas is kept constant at high concentration, a change interval where the concentration of the material gas changes from the high concentration to low concentration, and a final state interval where the concentration of the material gas is kept constant at the low concentration, the ratio between the first absorbance and the second absorbance is kept at 1:1/n at each time.

This is because the number of arms such as the methyl group is fixed in one organic metal. For example, in the case of trimethylgallium, three methyl groups are present for one gallium, and therefore as long as this relationship is not lost, values themselves of the absorbance change depending on the concentration of the material gas while keeping the ratio between the first absorbance and the second absorbance constant.

Figure 4C:
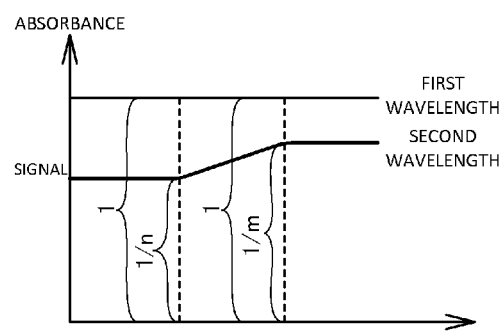

FIG. 4(c) illustrates a graph of pieces of time series data on the first and second absorbances measured when the semiconductor material self-decomposes during a state where the concentration of the material gas is kept constant. In an initial state interval, the semiconductor material does not self-decompose, and therefore as in FIG. 4(b), the ratio between the first absorbance and the second absorbance is kept at 1:1/n. On the other hand, when the semiconductor material self-decomposes, methane more easily absorbing light at the second wavelength than the semiconductor material is produced, and consequently a value of the second absorbance increases. At this time, concentration control is performed so as to keep the concentration of the material gas constant, and a gallium compound that is a product from the decomposed semiconductor material also absorbs light at a wavelength near the first wavelength. As a result, the first absorbance is kept substantially constant even when the self-decomposition occurs. That is, during the occurrence of the self-decomposition, an increase/decrease tendency is not the same between the first absorbance and the second absorbance, and consequently, the ratio between the first absorbance and the second absorbance at each time also changes.

As described, when the semiconductor material self-decomposes, the relationship in which the three methyl groups are present for one gallium is lost, and therefore even in the case where the first absorbance is kept constant as illustrated in FIG. 4(c), only the second absorbance changes. In this case, the ratio between the first absorbance and the second absorbance changes to a different ratio like 1:1/m.

Figure 3:
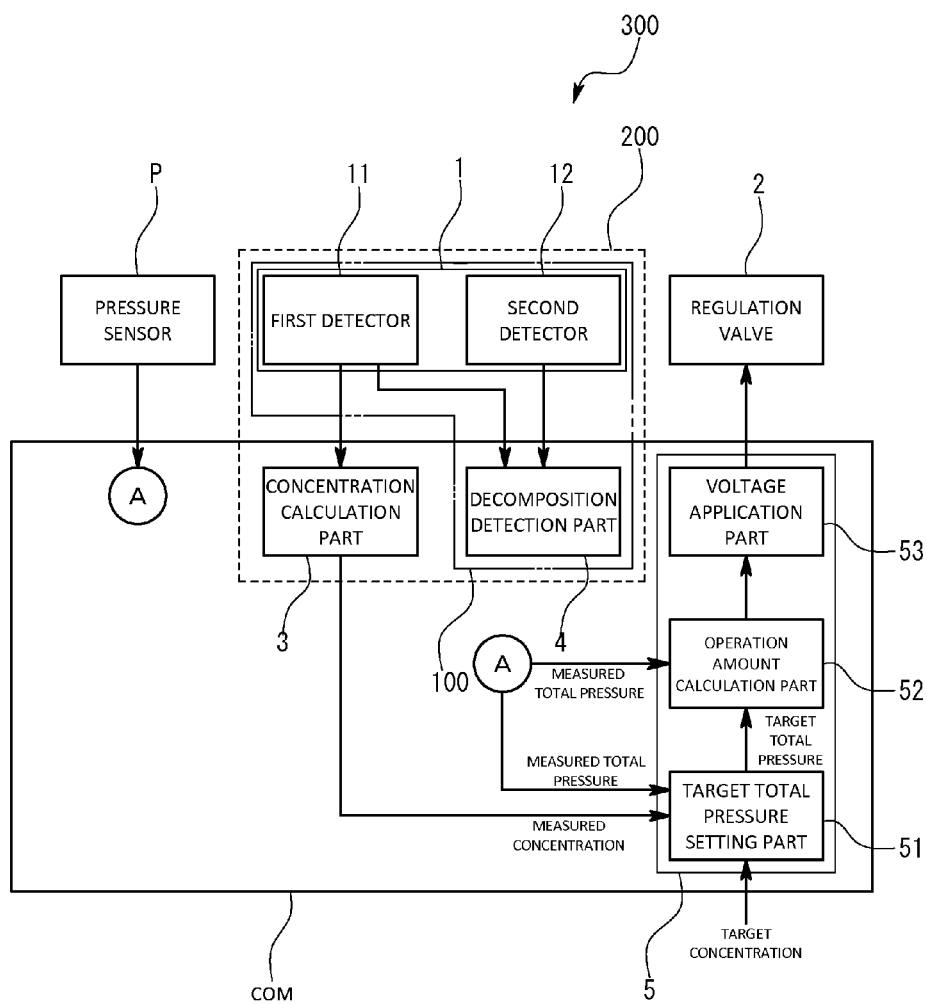
FIG. 3 is a schematic functional block diagram of the concentration control apparatus in the same embodiment.

The decomposition detection part 4 illustrated in FIG. 3 is one that on the basis of characteristics of the ratio between the first absorbance and the second absorbance as described above, detects whether or not the concentration of the material gas is changed, or whether or not the semiconductor material self-decomposes in the material gas. More specifically, the decomposition detection part 4 is configured to detect whether or not the self-decomposition occurs by comparing a value n of the ratio between the first absorbance and the second absorbance measured when the self-decomposition does not occur and a current value of the ratio between the first absorbance and the second absorbance. In the present embodiment, the decomposition detection part 4 is configured to perform the detection on the basis of the determination that when the current value of the ratio between the first absorbance and the second absorbance falls within an allowable range determined using the value n of the ratio between the first absorbance and the second absorbance determined in a state where the self-decomposition does not occur as a reference, the self-decomposition occurs. If the self-decomposition occurs, the decomposition detection part 4 alerts a user to check whether or not the bubbling system B and/or various settings have any problem.

The concentration calculation part 3 is one that on the basis of the Beer-Lambert law, calculates the concentration of the material gas in the mixed gas from measured first absorbance. Specifically, on the basis of the following expression, the measured concentration of the material gas is calculated.

$A(\lambda) = \epsilon(\lambda) \times C \times L$, where $A(\lambda)$ is absorbance at a wavelength $\lambda$, $\epsilon(\lambda)$ is an absorption coefficient at the wavelength $\lambda$, C is the concentration of the material gas, and L is an optical path length in the mixed gas.

Next the details of the valve control part 5 will be described.

The valve control part 5 is one that controls the opening level of the regulation valve 2 so as to keep the concentration of the material gas in the mixed gas constant at target concentration. Note that what the regulation valve 2 can control is not the concentration itself of the material gas but only the total pressure of the mixed gas. Also, among the concentration $C_z$ of the material gas, the partial pressure $P_z$ of the material gas, and the total pressure $P_t$ of the mixed gas, there is a relationship as expressed by the following expression.

$$C_z = P_z/P_t$$

The valve control part 5 is configured to control the opening level of the regulation valve 2 to control the total pressure $P_t$ utilizing the relational expression above and the fact that the regulation valve 2 can control the total pressure $P_t$, and consequently control the concentration $C_z$ of the material gas.

More specifically, when the measured concentration is lower than the target concentration, the valve control part 5 makes the opening level of the regulation valve 2 larger than a current opening level so as to decrease the total pressure $P_t$ as a denominator in order to increase the concentration. When the opening level of the regulation valve 2 is increased, the mixed gas more easily passes through the regulation valve 2, and therefore the amount of the mixed gas in the tank B1 and the lead-out pipe B3 decreases to reduce the total pressure $P_t$. The partial pressure $P_z$ of the material gas is substantially constant because it is equal to vapor pressure, and therefore it is obvious from the concentration expression that when the total pressure $P_t$ is reduced, the concentration of the material gas increases.

On the other hand, when the measured concentration is higher than the target concentration, the valve control part 5 makes the opening level of the regulation valve 2 smaller than a current opening level so as to increase $P_z$ as the denominator in order to reduce the concentration.

In order to achieve such actions in the valve control part 5, the valve control part 5 includes: a target total pressure setting part 51 adapted to set target total pressure on the basis of target concentration, measured concentration, and measured total pressure; an operation amount calculation part 52 adapted to calculate a voltage application amount, which is an operation amount, so as to minimize the deviation between the target total pressure set by the target total pressure setting part 51 and the measured total pressure measured by the pressure sensor P; and a voltage application part 53 adapted to change a voltage to be applied to the regulation valve 2 by an amount corresponding to the operation amount calculated by the operation amount calculation part 52.

Figure 5:
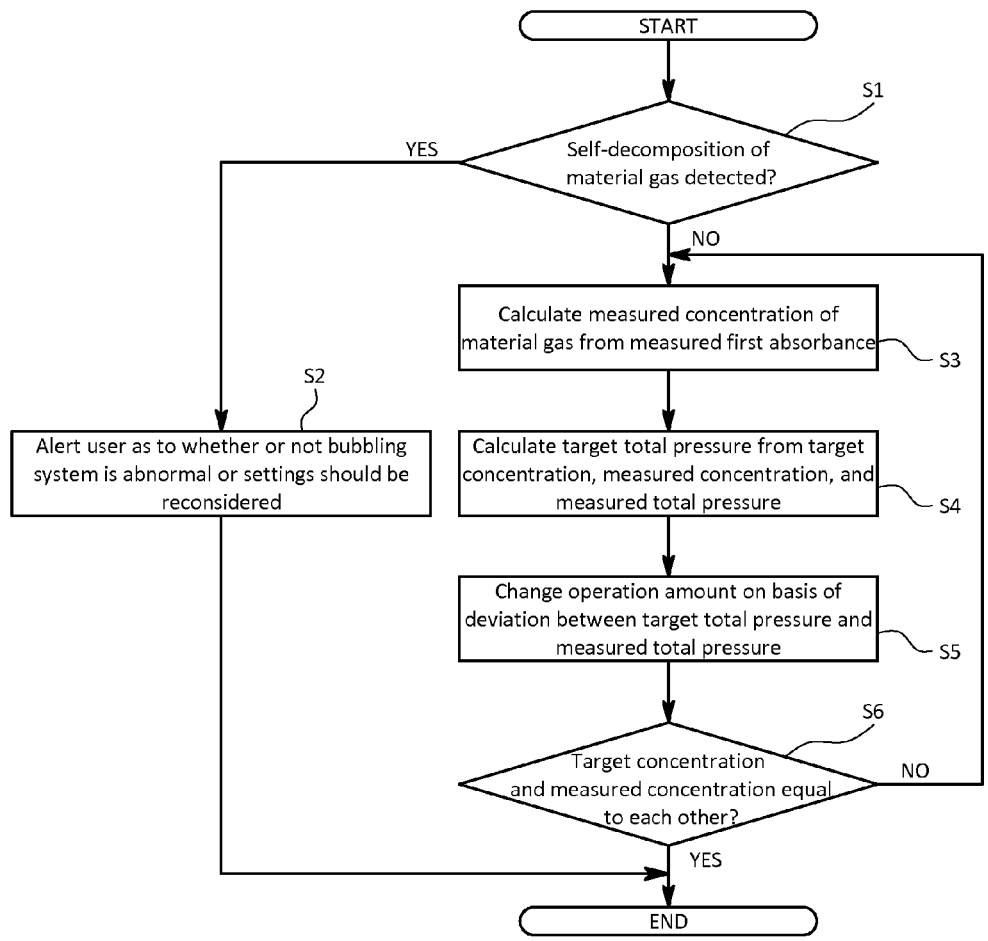
FIG. 5 is a flowchart illustrating the actions of the concentration control apparatus in the same embodiment.

Next, the actions of the concentration control apparatus 300 in the present embodiment will be described with reference to a flowchart in FIG. 5. Here, the configuration and actions of each of the parts constituting the valve control part 5 will be also described in detail.

First, in the decomposition detecting unit 100, on the basis of whether or not the value of the ratio between the first absorbance and the second absorbance is within a predetermined threshold value range, it is determined whether or not the material gas self-decomposes (Step S1).

In the case where in the decomposition detecting unit 100, the self-decomposition of the material gas is detected, a user is notified to check whether or not the bubbling system B is abnormal, or setting values such as a setting temperature inside the tank B1 are erroneous (step S2). Then, until a command to start concentration control is inputted after the user has completed the check, the concentration control apparatus 300 stops an action for the concentration control.

In the case where the self-decomposition of the material gas is not detected in the decomposition detecting unit 100, a routine for the concentration control is repeated.

More specifically, the concentration measuring unit 200 calculates the concentration $C_z$ of the material gas in the mixed gas from the first absorbance measured by the absorbance measuring mechanism 1 (Step S3).

Then, the target total pressure setting part 51 calculates the target total pressure on the basis of the following expression, and sets the calculated target total pressure for the operation amount calculation part 52 (Step S4).

$$P_{tr} = P_t \times (C_z / C_r)$$

Here, $P_{tr}$ is the target total pressure, $P_t$ the measured total pressure measured by the pressure sensor P, $C_z$ the measured concentration calculated by the concentration calculation part 3, and $C_r$ the target concentration.

Further, the operation amount calculation part 52 performs a feedback operation of the deviation between the target total pressure and the measured total pressure $P_t$ measured by the pressure sensor P to calculate an operation amount corresponding to a change in applied voltage to the regulation valve 2 (Step S5). The voltage application part 53 relatively changes the applied voltage from a current voltage correspondingly to the calculated operation amount to change the opening level of the regulation valve 2.

Also, in a predetermined control cycle, the target total pressure setting part 51 determines whether or not the target concentration and the measured concentration are equal to each other, and in the case where the both are equal to each other, current control is kept, whereas in the case where the both are not equal to each other, the actions in Step S3 to S5 are repeated to reregulate the opening level (Step S6).

In the concentration control apparatus 300 and the decomposition detecting unit 100 configured as described, since the decomposition detection part 4 is configured to, on the basis of the ratio between the first absorbance and the second absorbance, detect whether or not the self-decomposition occurs in the material gas, even in the case of a semiconductor material of which second absorbance is measurable regardless of whether or not self-decomposition occurs, like organic metal, a change in concentration of material gas and the self-decomposition can be distinguished from each other to detect only the self-decomposition.

Accordingly, in the case where the semiconductor material self-decomposes in the material gas, and concentration measurement or control may have some problem, a user can be notified of the problem and thereby take some measures. For this reason, even in the case of a semiconductor material likely to self-decompose, such as organic metal, it can be ensured that mixed gas can be supplied to a vacuum chamber with the concentration of material gas in mixed gas being kept accurate, and thereby reliability can be improved.

Also, since whether or not self-decomposition occurs can be detected only by measuring absorbances at two wavelengths, it is not necessary to use a large-sized and expensive measuring instrument such as an FTIR spectrometer. Further, an existing concentration measuring unit or concentration control apparatus is configured to be able to measure absorbance at least one wavelength in order to measure the concentration of material gas, and therefore only by making an addition to make it possible to measure absorbance at yet another wavelength, the decomposition detecting unit 100 in the present embodiment can be added to an existing bubbling system.

Still further, since the light source part 1B and the light detection part 1E of the absorbance measuring mechanism 1 can be provided for the lead-out pipe B3 and the measuring cell 1A in a contactless manner, even when heating the lead-out pipe B3 in order to prevent the condensation of material gas, the heat can be prevented from affecting the absorbance measuring mechanism 1. As a result, problems such as the erroneous detection of the self-decomposition in the material gas due to the effect of the heat can be preferably prevented.

The other embodiments will be described.

The semiconductor material is not limited to organic metal, but may be another semiconductor material. In short, the present invention can be applied to any other semiconductor material as long as the semiconductor material is vaporized and then used in a semiconductor manufacturing process and can self-decompose. Also, the semiconductor material is not limited to a liquid semiconductor material, but may also be a solid semiconductor material.

In the above-described embodiment, the decomposition detection part detects whether or not the material gas decomposes, on the basis of the ratio between the first absorbance and the second absorbance. However, the decomposition detection part may be configured to, on the basis of the ratio between first concentration calculated from the first absorbance and second concentration calculated from the second absorbance, detect whether or not the self-decomposition occurs. Also, the decomposition detection part does not use a value of the ratio, but may be configured to compare the ratio itself to detect whether or not the self-decomposition occurs. Further, the number of absorption wavelengths of a semiconductor material may be one, and the absorption wavelength is not required to be equal to an absorption wavelength of a material resulting from decomposition. That is, as the ratio between the first absorbance and the second absorbance, a ratio in the case where decomposition does not occur, and the second absorbance is zero may also be defined.

Figure 6A:
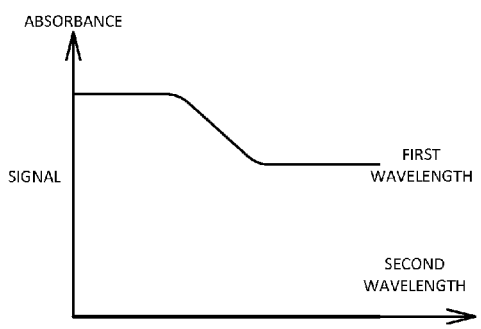
FIGS. 6(a) to 6(d) includes schematic graphs for explaining the relationship between absorbances and decomposition in other embodiments.
Figure 6B:
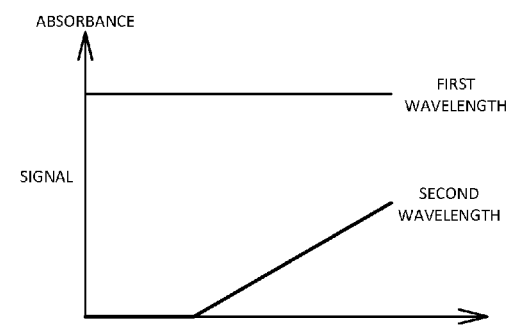

In the following, with reference to graphs of pieces of time series data on first absorbance and second absorbance illustrated in FIGS. 6(a) to 6(d), the detection of decomposition of a semiconductor material different from that in the above-described embodiment by the decomposition detection part will be described in more detail. FIGS. 6(a) and 6(b) illustrate graphs of the absorbances in the case where a light absorption wavelength of the semiconductor material and a light absorption wavelength of a material resulting from self-decomposition are not equal to each other. FIG. 6(a) illustrates a state where the concentration of material gas is controlled from a high concentration state to a low concentration state, and also illustrates changes in first absorbance and second absorbance in the case where self-decomposition does not occur.

As illustrated in FIG. 6(a), in the state where the decomposition does not occur, the material absorbing light at a second wavelength does not exist, and therefore the second absorbance is not measured by the absorbance measuring mechanism. As a result, only the first absorbance changes depending on a change in the concentration of the material gas. For example, in an interval where the concentration of the material gas is kept constant, the ratio between the first absorbance and the second absorbance is kept at 1:0, and therefore the decomposition detection part determines that the semiconductor material does not decompose.

FIG. 6(b) illustrates the case where the semiconductor material decomposes during a state where the concentration of the material gas is kept constant. When the semiconductor material decomposes, the first absorbance is kept, whereas the second absorbance increases along with the progress of the decomposition due to the newly produced material absorbing the light at the second wavelength. As described, the increase/decrease tendency of the first absorbance and that of the second absorbance are different, and the ratio between the first absorbance and the second absorbance also changes. As a result, the decomposition detection part can detect the decomposition on the basis of the first absorbance and the second absorbance.

Figure 6C:
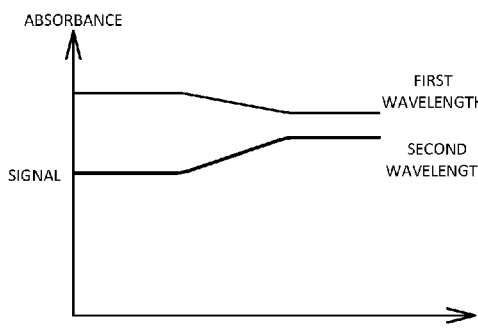
Figure 6D:
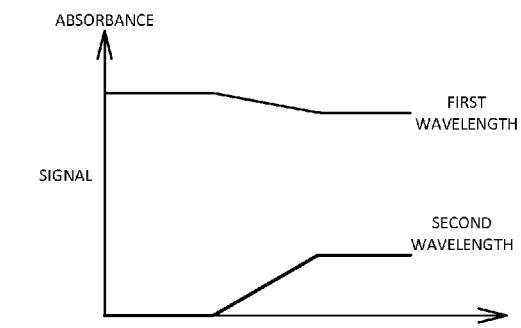

Further, FIG. 6(c) or 6(d) illustrates changes in first absorbance and second absorbance when a vaporized semiconductor material, which is further different from the above-described one, decomposes during a state where the concentration of material gas is controlled to be constant. In addition, in FIG. 6C or 6D, only in the intermediate interval where the second absorbance increases, the semiconductor material decomposes.

Even in the case of performing concentration control so as to keep the concentration of material gas constant during the occurrence of decomposition as illustrated in FIGS. 4(c) and 6(b), first absorbance may reduce. Even in such a case, it turns out from FIG. 6(c) or 6(d) that when the decomposition occurs, the ratio and difference between the first and second absorbances, and the increase/decrease tendencies of the first and second absorbances change as compared with before the occurrence of the decomposition of the semiconductor material. Accordingly, the decomposition detection part can detect the decomposition of the semiconductor material by comparing the first absorbance and the second absorbance with each other.

The decomposition detection part is not limited to one that compares the ratio between the first absorbance and the second absorbance to detect the decomposition of the semiconductor material, but may be one that detects the decomposition of the semiconductor material on the basis of the first absorbance and the second absorbance.

For example, the decomposition detection part may be configured to detect the decomposition of the semiconductor material on the basis of a result of comparing the difference between the first absorbance and the second absorbance measured when the semiconductor material does not decompose and the current difference between the first absorbance and the second absorbance with each other. Even in the case where the decomposition detection part compares the difference between the first absorbance and the second absorbance, as can be seen from the examples in FIGS. 4(a) to 4(c) and FIGS. 6(a) to 6(d), the difference significantly changes at the time of decomposition, and therefore the decomposition can be detected.

Also, the decomposition detection part may be configured to detect the decomposition of the semiconductor material when the increase/decrease tendency of the first absorbance and the increase/decrease tendency of the second absorbance at the same time are different from each other. For example, it is only necessary that the decomposition detection part is configured to differentiate the time series data on the first absorbance and the time series data on the second absorbance, and when resulting signs are not the same and therefore the increase/decrease tendencies of them are different from each other, determine that the decomposition occurs. Even in such a configuration, for example, as can be seen from the example in FIG. 4(c), when the decomposition occurs, the first absorbance does not exhibit any increase or decrease, whereas the second absorbance tends to increase, and therefore the occurrence of the decomposition can be detected because of the different increase/decrease tendencies.

Figure 7:
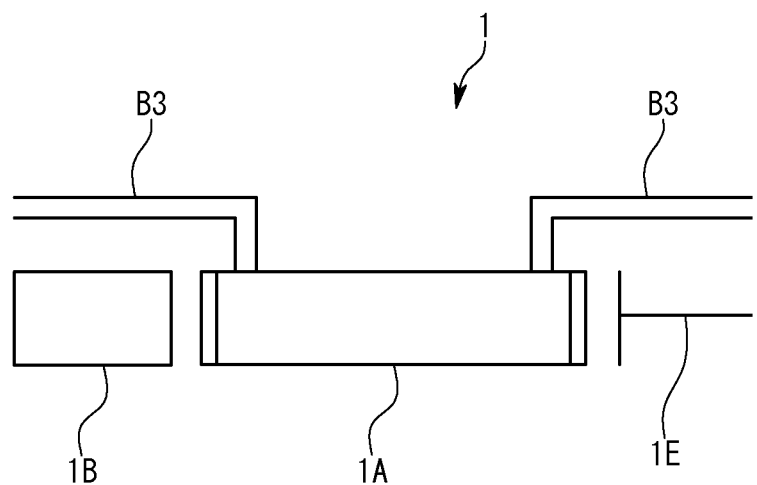
FIG. 7 is a schematic diagram illustrating the details of an absorbance measuring mechanism in still another embodiment.

The absorbance measuring mechanism is not limited to one of an NDIR type, but may be one of a laser absorption spectroscopy type. More specifically, as illustrated in FIG. 7, the absorption measuring mechanism 1 may be a laser absorption spectroscopy type gas analyzer including: a measuring cell 1A through which the mixed gas passes, a light source part 1B that, to the measuring cell, emits a laser beam having a wavelength at which the semiconductor material absorbs light, and a laser beam having a wavelength at which the material produced when the semiconductor material decomposes absorbs light; and a light detector 1E that detects the beams having passed through the measuring cell 1A. As the light source part 1B, multiple laser light sources may be prepared, or one laser light source capable of emitting laser beams having multiple wavelengths may be used.

Similarly, even the absorbance measuring mechanism of an NDIR type may be adapted to measure first absorbance and second absorbance using multiple light sources. In addition, the absorbance measuring mechanism may be configured to, depending on a semiconductor material, measure three or more absorbances, and thereby detect decomposition.

The concentration control apparatus may be configured to control the opening level of the regulation valve on the basis of the deviation between the target concentration and the measured concentration.

The concentration measuring unit and the decomposition detecting unit in the above-described embodiment are not limited to ones for a bubbling system, but can be used for various purposes. That is, the decomposition detecting unit may detect whether or not in mixed gas containing at least material gas resulting from the vaporization of a semiconductor material, decomposition occurs in the material gas.

The decomposition of material gas is not limited to self-decomposition but may include various types of decomposition. For example, in the case of using tungsten fluoride as a semiconductor material, a decomposition reaction in which tungsten fluoride reacts with water to produce hydrogen fluoride takes place. The decomposition detecting unit of the present invention may be configured to detect such decomposition.

The absorbance measuring mechanism is not limited to one of an NDIR type, but only required to be a measuring instrument that can measure absorbances at two wavelengths. An FTIR spectrometer may be used if budget and space allow.

Besides, various modifications and combinations of the embodiments may be made without departing from the scope of the present invention.

REFERENCE SIGNS LIST

300: Concentration control apparatus
200: Concentration measuring unit
100: Decomposition detecting unit
1: Absorbance measuring mechanism
2: Regulation valve
P: Pressure sensor
COM: Control mechanism
3: Concentration calculation part
4: Decomposition detection part
5: Valve control part
51: Target total pressure setting part
52: Operation amount calculation part
53: Voltage application part
B: Bubbling system
B1: Tank
B2: Introduction pipe
B3: Lead-out pipe

The invention claimed is:

1. A decomposition detecting unit comprising:
a gas analyzer, that is an NDIR gas analyzer or laser absorption spectroscopic gas analyzer, that measures first absorbance and second absorbance of mixed gas containing material gas resulting from vaporization of a semiconductor material, the first absorbance being absorbance at a wavelength at which the semiconductor material absorbs light, the second absorbance being absorbance at a wavelength at which a material produced when the semiconductor material decomposes absorbs light; and
a decomposition detector that detects the decomposition of the semiconductor material on a basis of the first absorbance and the second absorbance.

2. The decomposition detecting unit according to claim 1, wherein
the decomposition detector is configured to detect the decomposition of the semiconductor material on a basis of a result of comparing a ratio between the first absorbance and the second absorbance measured when the semiconductor material does not decompose and a current ratio between the first absorbance and the second absorbance.

3. The decomposition detecting unit according to claim 1, wherein
the decomposition detector is configured to detect the decomposition of the semiconductor material on a basis of a result of comparing a difference between the first absorbance and the second absorbance measured when the semiconductor material does not decompose and a current difference between the first absorbance and the second absorbance.

4. The decomposition detecting unit according to claim 1, wherein
the decomposition detector is configured to detect the decomposition of the semiconductor material when a respective trend of each of the first and second absorbances at the same time are different, the respective trends being one of an increase, a decrease, or no change.

5. The decomposition detecting unit according to claim 1, wherein
the gas analyzer is the NDIR gas analyzer and comprises:
a measuring cell through which the mixed gas passes;
a light source that emits light having a predetermined wavelength bandwidth to the measuring cell;
a first filter that allows passing of, among light having passed through the measuring cell, light having the wavelength at which the semiconductor material absorbs light;
a second filter that allows passing of, among the light having passed through the measuring cell, light having the wavelength at which the material produced when the semiconductor material decompose absorbs light; and
a light detector that detects the light having passed through the first filter or the second filter.

6. The decomposition detecting unit according to claim 1, wherein
the gas analyzer is the laser absorption spectroscopic gas analyzer and comprises:
a measuring cell through which the mixed gas passes;
a light source that, to the measuring cell, emits a laser beam having the wavelength at which the semiconductor material absorbs light, and a laser beam having the wavelength at which the material produced when the semiconductor material decomposes absorbs light; and
a light detector that detects the laser beams having passed through the measuring cell.

7. The decomposition detecting unit according to claim 1, wherein
the semiconductor material is organic metal.

8. A concentration measuring unit comprising:
the decomposition detecting unit according to claim 1, and
a concentration calculator that on a basis of the first absorbance, calculates concentration of the material gas in the mixed gas.

9. A concentration control apparatus that is used for a bubbling system comprising:
a tank adapted to contain a semiconductor material; an introduction pipe adapted to introduce carrier gas into the tank; and a lead-out pipe adapted to lead mixed gas containing the material gas and the carrier gas out of the tank, the concentration control apparatus comprising:
the concentration measuring unit according to claim 8;
a regulation valve that is provided in the lead-out pipe; and
a valve controller that controls the regulation valve on a basis of preset target concentration and measured concentration of the material gas, the measured concentration being measured by the concentration measuring unit.

* * * * *